(12) United States Patent
Stephani et al.

(10) Patent No.: US 8,952,343 B2
(45) Date of Patent: Feb. 10, 2015

(54) SYSTEM AND METHOD FOR AUTOMATED CYCLOTRON PROCEDURES

(71) Applicant: Varian Medical Systems Particle Therapy GmbH, Bergisch-Gladcach, DE (US)

(72) Inventors: Thomas Stephani, Bergisch Gladback (DE); Uwe Behrens, Hamburg (DE); Heinrich Roecken, Bonn (DE); Jan Timmer, Cologne (FR); Christian Baumgarten, Untersiggenthal (DE)

(73) Assignee: Varian Medical Systems Particle Therapy GmbH, Bergisch-Gladbach (DE)

( * ) Notice: Subject to any disclaimer, the term of this patent is extended or adjusted under 35 U.S.C. 154(b) by 0 days.

(21) Appl. No.: 13/887,071

(22) Filed: May 3, 2013

(65) Prior Publication Data
US 2013/0303824 A1    Nov. 14, 2013

Related U.S. Application Data

(63) Continuation of application No. 13/225,045, filed on Sep. 2, 2011, now Pat. No. 8,440,987.

(60) Provisional application No. 61/380,017, filed on Sep. 3, 2010.

(51) Int. Cl.
*A61N 5/10* (2006.01)
*H05H 7/02* (2006.01)
(Continued)

(52) U.S. Cl.
CPC .. *H05H 7/02* (2013.01); *H01J 3/14* (2013.01); *H05H 13/005* (2013.01); *A61N 5/1077* (2013.01); *A61N 5/10* (2013.01); *H05H 2007/122* (2013.01); *H05H 2277/11* (2013.01); *A61N 2005/1087* (2013.01)
USPC .............. 250/492.22; 250/492.23; 250/492.1; 250/492.3; 315/502

(58) Field of Classification Search
USPC .................. 250/396 R, 492.1, 492.3, 492.21, 250/492.22, 492.23, 505.1; 315/500, 502; 378/65; 312/62; 324/71.3, 71.4
See application file for complete search history.

(56) References Cited

U.S. PATENT DOCUMENTS

| 5,363,008 A | 11/1994 | Hiramoto et al. |
| 6,717,162 B1 | 4/2004 | Jongen |

(Continued)

OTHER PUBLICATIONS

Timmer, et al. "Automated Cyclotron Tuning Using Beam Phase Measurements." Nuclear Instruments and Method in Physics Research Dec. 1, 2006 vol. 568 No. 2 pp. 532-536.

(Continued)

*Primary Examiner* — Bernard E Souw (57) ABSTRACT

Systems and methods are provided to perform efficient, automatic cyclotron initialization, calibration, and beam adjustment. A process is provided that allows the automation of the initialization of a cyclotron after overnight or maintenance imposed shutdown. In one embodiment, five independent cyclotron system states are defined and the transition between one state to another may be automated, e.g., by the control system of the cyclotron. According to these embodiments, it is thereby possible to achieve beam operation after shutdown with minimal manual input. By applying an automatic procedure, all active devices of the cyclotron (e.g., RF system, extraction deflectors, ion source) are respectively ramped to predefined parameters.

36 Claims, 5 Drawing Sheets

(51) Int. Cl.
    *H01J 3/14* (2006.01)
    *H05H 13/00* (2006.01)
    *H05H 7/12* (2006.01)

(56) References Cited

U.S. PATENT DOCUMENTS

| | | | | |
|---|---|---|---|---|
| 8,039,822 | B2* | 10/2011 | Rietzel | 250/492.3 |
| 8,440,987 | B2* | 5/2013 | Stephani et al. | 250/492.22 |
| 8,445,872 | B2* | 5/2013 | Behrens et al. | 250/492.22 |
| 2009/0230327 | A1* | 9/2009 | Rietzel | 250/492.3 |
| 2009/0236545 | A1 | 9/2009 | Timmer | |
| 2012/0056099 | A1 | 3/2012 | Behrens et al. | |
| 2013/0077569 | A1* | 3/2013 | Nam et al. | 370/328 |

OTHER PUBLICATIONS

Geisler, et al, "Commissioning of the Accel 250 MEV Proto Cyclotron." Cyclotrons and Their Applications 2007, pp. 9-14.

* cited by examiner

SYSTEM AND METHOD FOR AUTOMATED CYCLOTRON PROCEDURES

CLAIM OF PRIORITY

This application is a continuation of U.S. patent application Ser. No. 13/225,045, filed Sep. 2, 2011 both claiming the benefit of U.S. Provisional Application No. 61/380,017, filed Sep. 3, 2010, and is also related to co-pending U.S. patent application entitled "SYSTEM AND METHOD FOR LAYER-WISE PROTON BEAM CURRENT VARIATION" Ser. No. 13/887,071, filed on the same day herewith and U.S. patent application Ser. No. 13/224,773, filed Sep. 2, 2011. Each of these references is incorporated by reference herein in their entireties and for all purposes.

TECHNICAL BACKGROUND

Radiation therapy (RT) is a popular and efficient method for cancer treatment, where ionizing radiation is used in an attempt to destroy malignant tumor cells or to slow down their growth. RT is often combined with surgery, chemotherapy, or hormone therapy, but may also be used as a primary therapy mode. Radiation therapy is most commonly administered as external beam RT, which typically involves directing beams of radiated particles produced by sources located externally with respect to the patient or subject to the afflicted treatment area. The beam can consist of photons, electrons, protons or other heavy ions. As the beam travels through matter (e.g., the subject), energy from the ionizing radiation is deposited along the path in the surrounding matter. This energy is known as "dose," and is used to measure the efficacy and accuracy of a radiation beam. Malignant cells are damaged along the path of radiation beam during the RT. Unfortunately, the damage from the radiation is not limited to malignant cells and may be incurred by any interceding or adjacent cells. Thus, the dosage of radiation to healthy tissues outside the treatment volume is ideally minimized to avoid being collaterally damaged.

Proton therapy is one type of external beam radiation therapy, and is characterized for using a beam of protons to irradiate diseased tissue. The chief advantage of proton therapy over other conventional therapies such as X-ray or neutron radiation therapies is the ability to administer treatment dosages three dimensionally, by specifying the depth (i.e., penetration) of applied radiation, thereby limiting the inadvertent exposure of un-targeted cells to the potentially harmful radiation. This enables proton therapy treatments to more precisely localize the radiation dosage when compared with other types of external beam radiotherapy. During proton therapy treatment, a particle accelerator, such as a cyclotron, is used to generate a beam of protons from, e.g., an internal ion source located in the center of the cyclotron. The protons in the beam are accelerated—via a generated electric field—and a beam of accelerated protons is subsequently "extracted," magnetically directed through a series of interconnecting tubes (called the beamline), and applied to a subject in a target treatment room.

Customarily, cyclotron maintenance procedures are performed during services and repairs. Additionally, due to its high consumptive energy usage during operation, a common practice is to shut down or keep a cyclotron in a reduced power state at the end of each day of operation. Conventionally, the re-initialization of cyclotrons after these customary overnight shut-downs or after a service action is completed was performed completely manually by an operator. Among the re-initialization procedures, the operator has to vary the magnetic field of the cyclotron by varying the current of the main coil within the cyclotron to generate a proton beam and to determine a stable working point of the cyclotron. Due to thermal drifts of the cyclotron iron, the magnet current must also be adjusted manually in regular intervals.

Additional readjustments of cyclotrons are also typically required after a service action or repair is performed. These readjustments typically include reconfiguring and re-arranging moveable components within the cyclotron based on analyzed performance values. Generally, these readjustments are performed manually, and also require even well-trained technicians a considerable amount of time.

Unfortunately, due to the complexity of the underlying machines, their operating and maintenance procedures, and the gravity of the corresponding medical procedures, highly trained and skilled operators are needed to perform each of these procedures. Naturally, this can result in significant inefficiency, delay or even potential hazards if qualified operators are not available.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

To overcome the difficulties inherent in traditional, manual proton therapy system initialization, calibration, and beam adjustment methods, new techniques for automating these procedures are herein provided. A process is provided that allows the automation of the initialization of a proton therapy system—such as a cyclotron—after overnight or maintenance imposed shutdown. In one embodiment, five independent cyclotron system states are defined and the transition between one state to another may be automated, e.g., by the control system of the cyclotron. According to these embodiments, it is thereby possible to achieve beam operation after shutdown with minimal manual input. By applying an automatic procedure, all active devices of the cyclotron (e.g., a radio-frequency or "RF" system, extraction deflectors, ion source) are respectively ramped to predefined parameters.

In one embodiment, automating the initialization procedures of a cyclotron may be performed by calculating the current set value of the main magnet of the cyclotron as a function of the cyclotron iron temperature. This allows a proton beam to be extracted out of the cyclotron directly at the end of the start-up procedure without the performance of any additional procedures. Additionally, the working point of the cyclotron is tuned by an automated phase control loop to guarantee the beam quality needed for medical operation of the system. The phase control loop tunes the magnetic field to an optimal level by analyzing and stabilizing the phase shift of the extracted beam with respect to the RF frequency of the cyclotron measured by a phase measurement system.

According to a second aspect of the invention, a system and methods are provided which allow calibration procedures to be automatically performed by the control system of the cyclotron to allow less skilled personnel to calibrate the cyclotron and to ensure the calibration is performed correctly.

These procedures may include performing beam centering by calculating the set values for the positions of the inner trim rods or for the operating currents of the trim coils of the cyclotron by analyzing the radial behavior of the cyclotron's internal beam current measured with an internal straight beam or radial beam probe. Another calibration procedure may include increasing the extraction efficiency by automatically analyzing the extracted beam current as influenced by the settings of the cyclotron's central chamber of components. Specifically, the outer trim rods or extraction trim coils, and the voltages applied to one or more extraction deflectors.

Also disposed within a central chamber of the cyclotron are a plurality of phase slits used to modulate the extracted beam current. To further improve a cyclotron's efficiency by reducing internal beam losses, the operative radial positions of the phase slits may also be automatically determined by analyzing the phase slit transmission curves of the cyclotron with respect to defined position criteria. In one embodiment, each of these calibration steps may be performed automatically by the control system of the cyclotron. Thus, the operative settings can be determined without verification or oversight of highly skilled personnel.

BRIEF DESCRIPTION OF DRAWINGS

The accompanying drawings, which are incorporated in and form a part of this specification, illustrate embodiments of the invention and, together with the description, serve to explain the principles of the invention.

DETAILED DESCRIPTION

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, and components, have not been described in detail as not to unnecessarily obscure aspects and features of the subject matter.

Portions of the detailed description that follows are presented and discussed in terms of a method. Although steps and sequencing thereof are disclosed in figures herein (e.g., FIGS. 4, and 5) describing the operations of this method, such steps and sequencing are exemplary. Embodiments are well suited to performing various other steps or variations of the steps recited in the flowchart of the figure herein, and in a sequence other than that depicted and described herein.

Exemplary Proton Accelerator

Figure 1:
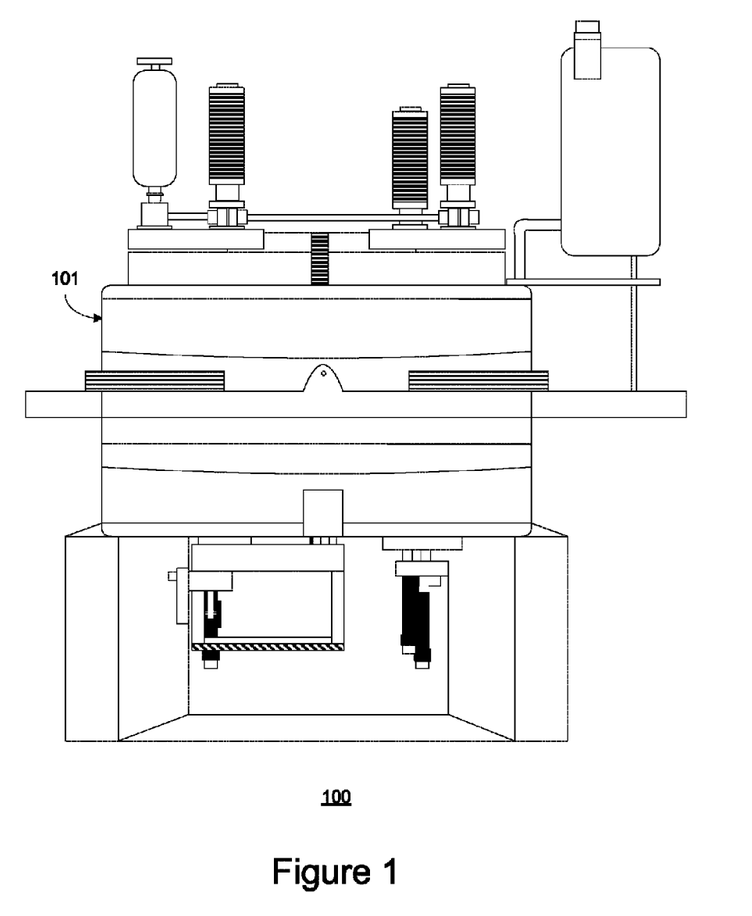
FIG. 1 depicts a diagram of an exemplary proton accelerator, in accordance with various embodiments of the claimed subject matter.

With reference now to FIG. 1, an illustration of an exemplary proton accelerator 100 is depicted, in accordance with one embodiment. In one configuration, the proton accelerator 100 may be implemented as a cyclotron. In further embodiments, the cyclotron may be, for example, a compact four sector isochronous cyclotron incorporating a superconducting main coil magnet. As depicted, the superconducting main coil may be housed in a central chamber 101, in which particles of a generated proton beam from an ion source are accelerated on radially increasing trajectories. In an exemplary configuration, the cyclotron operates with a beam energy of 250 MeV, and is capable of generating a maximum beam current of about 800 nA with a typical extraction efficiency of 80%.

Figure 2:
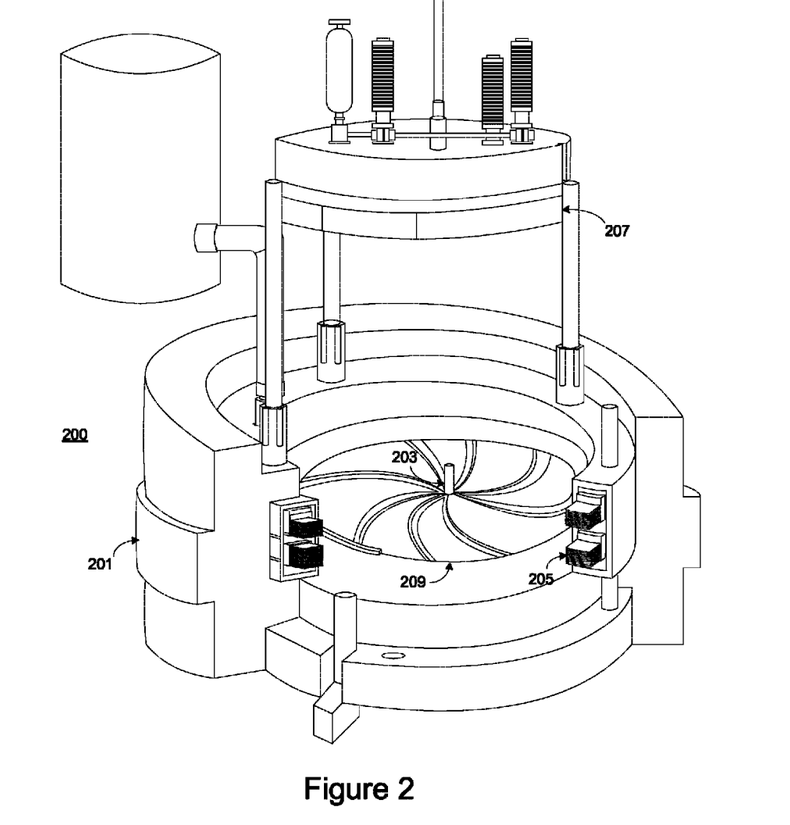
FIG. 2 depicts an expanded-view diagram of an exemplary proton accelerator, in accordance with various embodiments of the claimed subject matter.

With reference now to FIG. 2, an illustration of an expanded-view diagram of an exemplary proton accelerator 200 is depicted, in accordance with various embodiments of the claimed subject matter. The exemplary proton accelerator 200 may, for example, be implemented as the cyclotron described above with reference to FIG. 1. As depicted, FIG. 2 depicts the upper portion of a cyclotron 200 with a raised top 207 (typical during the performance of a service action or during maintenance procedures, for example). A beam of protons is generated in a central chamber 209 by an ion source 203, and, while being accelerated by a radio-frequency driven sub-system, is guided to the extraction radius in a spiral-like form by the magnetic field induced by the superconducting magnet (depicted, in part, as a portion of a main coil 205).

According to some embodiments, operation of a cyclotron to generate a proton beam for proton therapy may comprise a plurality of component sub-systems working in concert. These sub-systems may have dedicated functionalities and may include (but is not limited to): a super-conducting magnet sub-system, which includes the super-conducting magnet 205 and the control system thereof; a cryogenic-cooling sub-system and the control system thereof which maintains the thermal stability of the components of the cyclotron, such as the super-conducting magnet 205, and/or the temperature within the central chamber 209 of the cyclotron; a vacuum sub-system and the control system thereof for maintaining a pressure within the central chamber 209 of the cyclotron; a radio-frequency sub-system and the control system thereof for providing alternating electrical fields which accelerate the protons up to their target energy (e.g. 250 MeV), and an ion source and the control system thereof for generating a plurality of protons which comprises the proton beam.

In further embodiments, the plurality of component sub-systems also includes a vertical deflector plate sub-system, and the control system thereof, for generating an electric field that may be used to turn the beam on or off and to adjust the beam intensity of a generated proton beam. Additionally, the plurality of component sub-systems may also include a feedback sub-system and the control system thereof for monitoring a proton beam extracted from the cyclotron. According to some embodiments, the feedback sub-system may be configured to measure and quantify the effect of beam phase shifts incurred by the proton beam due to drifts in the magnetic fields generated by the magnetic sub-system 205. Measurement and analysis of the beam phase shifts may be performed by, for example, a non-destructive beam phase detector disposed in the cyclotron. In still further embodiments, the feedback sub-system may also include a phase control loop configured to monitor and calibrate an extracted proton beam by, for example, tuning a magnetic field generated by the super-conducting magnet sub-system 205 system by measuring the effect of the beam phase shifts affecting the proton beam with respect to a radio frequency generated by the radio frequency sub-system during operation of the cyclotron. Additionally, the feedback sub-system may also perform tuning of the extraction efficiency and beam current stability for the proton beams produced by the cyclotron.

According to one embodiment, the component sub-systems each have an individual power state. These power states allow the sub-systems to be powered on, off, or operate at reduced power levels independent from each other. Powering off of one or more sub-systems may be required during maintenance, service, or daily shutdown procedures, for example. According to further embodiments, one or more of the component sub-systems may have power states that depend on the power state of another component sub-system, and therefore, powering a sub-system on (or off) may required being performed in a particular sequence. For example, an ion source may require the vacuum sub-system to be operational before the ion source is able to achieve an operational state capable of generating particles.

After an overnight or maintenance imposed shutdown, initialization of the cyclotron 200 may be performed. In one embodiment, a plurality of independent cyclotron system states are defined and the transition between one state to another in a sequence (which can be more than one particular sequence) is completely automated. The transition between the cyclotron system states may, for example, be performed according to an automatic procedure applied by the control system of the cyclotron 200. The automatic procedure may provide a sequence during which all active devices of the cyclotron (e.g., RF system, extraction deflectors, ion source) are respectively ramped to predefined parameters. According to these embodiments, it is thereby possible to achieve beam operation after shutdown with minimal manual input.

Figure 3:
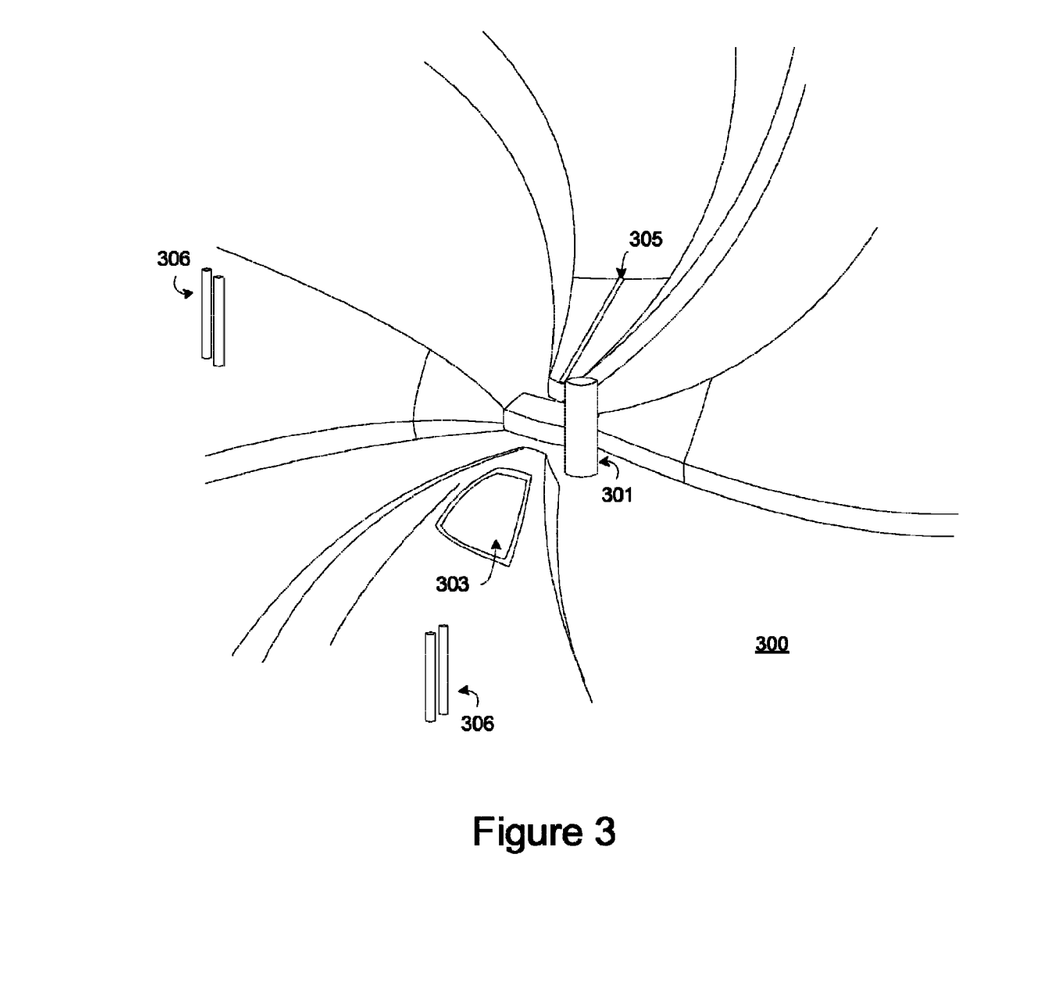
FIG. 3 depicts an illustration of a portion of a central chamber in an exemplary proton accelerator, in accordance with various embodiments of the claimed subject matter.

FIG. 3 depicts a close-up illustration of a portion of the central chamber 300 (e.g., central chamber 209) in an exemplary proton accelerator (e.g., cyclotron 100 and 200), in accordance with various embodiments of the claimed subject matter. The portion of the central chamber 300 depicted in FIG. 3 includes an internal ion source 301, an electrostatic vertical deflector plate 303, a vertical collimator bracket 305. According to one embodiment, during a proton therapy treatment session, a proton beam emanates as a stream or burst of protons from the ion source 301, the stream (or burst) of protons is accelerated by electrical fields of the radio frequency (RF) sub-system and guided to the extraction radius in a spiral form via the magnetic field in the central chamber 300 produced by magnetic coils (e.g., magnetic coils 205).

The produced proton beam is then threaded through one or more phase slits (e.g., phase slit 306), resulting in an extracted proton beam having a corresponding beam current. As presented, the phase slits 306 include apertures through which the proton beam travels. In one embodiment, the size of the aperture of a phase slit 306 is of sufficient size to allow a generated proton beam to traverse completely unimpeded. According to alternate embodiments, the size of the aperture of the phase slit 306 is less than that of a complete proton beam, such that at least a portion of any generated proton beam is absorbed by the material of the phase slit 306 when the proton beam is travelling through the aperture.

Calibrating the proton beam (and by extension, the beam current of an extracted beam) may be thus performed by producing a voltage in the electrostatic vertical deflector 303, thereby producing an electric field. The properties imparted by the electric field affect the particles comprised in the beam of protons, and is capable of influencing the trajectory of the produced proton beam. A stronger electric field produces a greater influence, and thus, the proton beam is capable of being aimed to the extent that the trajectory of the proton beam is at least partially directed into (and thus, intercepted by) the vertical collimator 305 by running varying voltages through the electrostatic vertical deflector 303. For example, in one embodiment, a maximum beam current may correspond to little or no voltage in the electrostatic vertical deflector 303, thereby leaving most if not all of the produced beam through the aperture unimpeded.

The transmitted beam of the vertical deflector and collimator systems will be guided to the phase slits 306. According to one embodiment, the opening widths of the phase slits are variable and a portion of the proton beam could be stopped by this measure. If the apertures of the phase slits are completely open, the transmitted beam by the vertical deflector and collimator systems and the extracted beam may have approximately the same beam current (only influenced by the extraction efficiency of the cyclotron). The magnitude of the electric field of the vertical deflector 303 may be controlled by applying smaller or larger voltages to the electrostatic vertical deflector 303. The portion of the proton beam that travels through the apertures of the vertical collimator 305 and the phase slits 306 has a decreased beam current with an intensity lowered by an amount which corresponds to the portion of the produced proton beam intercepted by the non-aperture portion of the vertical collimator 305 and the phase slits 306.

Automated Initialization of Superconducting Proton Cyclotron

After an overnight or maintenance imposed shutdown, initialization of a cyclotron may be required in order for the cyclotron to achieve operational levels. The transition between the cyclotron system states may, for example, be performed according to an automatic sequence or cycle and applied by the control system of the cyclotron. Each cyclotron system state corresponds to a frequently used system state, and defines the operational (or "power") state of each sub-system of the cyclotron's operation. The automatic procedure may provide a sequence during which all active devices of the cyclotron (e.g., RF system, extraction deflectors, ion source) are respectively ramped to predefined parameters. According to these embodiments, it is thereby possible to achieve beam operation after shutdown with minimal manual input.

Figure 4:
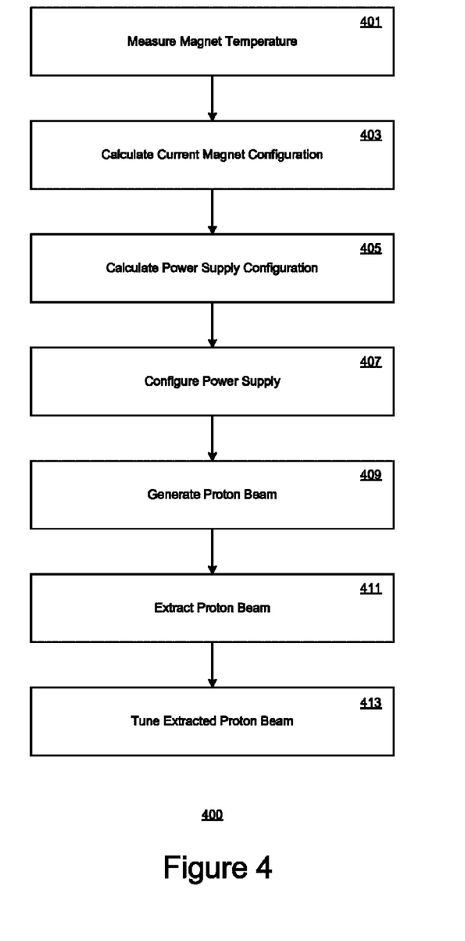
FIG. 4 depicts a flowchart of a method of automatically initializing a proton accelerator, in accordance with embodiments of the claimed subject matter.

FIG. 4 depicts an example procedure 400 wherein five independent cyclotron system states are defined and the transition between one state to another in sequence is partially or completely automated. The transition between these states may be performed to initialize a cyclotron in preparation for operation, or to variably shutdown or deactivate all or portions of the cyclotron in anticipation of a overnight shutdown, service procedure, or lengthy deactivation. Steps 401-413 describe exemplary steps of the process 400 in accordance with the various embodiments herein described.

In one embodiment, the five cyclotron states may be characterized as "Off"; "Standby 1"; "Standby 2"; "RF Ready"; and "Beam Ready." The cyclotron state Off may be implemented to completely deactivate (power off) all component sub-systems of the cyclotron, and may be used when the cyclotron must be opened and is non-operational, such as during a service routine. In alternate embodiments, the cyclotron state "Off" may be implemented to deactivate all component sub-systems except for the cryogenic cooling sub-systems, The cyclotron state "Standby 1" may be implemented to evacuate the cyclotron using the vacuum control system, but de-activate (or maintain deactivation of) the remaining sub-systems of the cyclotron. In further embodiments, the super-conducting magnet sub-system may operate in a reduced power state during the cyclotron state Standby 1. Standby 1 may be used, for example, when the cyclotron is closed and evacuated, such as when longer shutdown periods are expected. Transitioning between the Off and Standby 1 (and vice versa) cyclotron states may be performed automatically through the control terminal of the cyclotron.

Cyclotron state Standby 2 may be used during overnight shutdowns, such as at the end of daily operation to reduce the consumption of energy usage. During Standby 2, the cryogenic-cooling sub-system, the super-conducting magnet sub-system, and the vacuum sub-system are active with the remaining sub-systems deactivated and non-operational. To maintain the thermal stability of the magnet iron and other cyclotron parts, the cooling water of various sub-systems may be set to an increased temperature between Standby 1 and Standby 2. This also has the effect of minimizing transient effects caused by heating from radio frequency losses when returning to standard beam operation. Starting from Standby 2, beam operation may be possible within minutes, according to embodiments of the claimed subject matter. With the automated transition to the cyclotron state RF Ready, the radio frequency amplifier is switched on and the RF sub-system is set to operation. Conversely, when transitioning from RF Ready to Standby 2, the radio frequency amplifier is switched off and the RF sub-system is deactivated. In one embodiment, the RF sub-system operates at a reduced power state in the cyclotron state RF Ready, and may be used as an alternate overnight shutdown state, or during short standby periods (e.g., between procedures). In further embodiments, the reduced power state of the RF sub-system operates at about 50% of its maximum power. A subsequent transition to the state Beam Ready sets the remaining components (e.g., ion source, extraction deflectors, vertical deflector and feedback sub-systems) to pre-defined default values as well as increasing the power state of the RF sub-system to a standard beam ready state.

An automatic initialization procedure may be performed by automatically cycling through the cyclotron states in sequence, such as the sequence according to process 400 of FIG. 4. According to process 400, the temperature of a super-conducting magnet in the super-conducting magnet sub-system of a cyclotron is measured at step 401. The temperature of the super-conducting magnet may be measured by, for example, measuring the temperature of the iron comprising the super-conducting magnet. According to alternate embodiments, the temperature of various components of the super-conducting magnet (e.g., the magnet coils 205) may be measured. Once the temperature of the cyclotron iron is determined, the current configuration of the main magnet of the cyclotron is calculated at step 403 as a function of the measured iron temperature. A configuration of the power supply required to bring the cyclotron to standard operational state is then determined at step 405. For example, a low iron temperature measured in step 401 corresponds to a reduced current setpoint of the magnet. If such a current setpoint is calculated, the power-supply may be instructed to reduce the current of the cyclotron magnet, automatically bringing the super-conducting magnet sub-system to standard operational settings. Conversely, if the iron temperature already corresponds to standard operational temperatures, no change may be performed in the power-supply configuration. The power-supply of the super-conducting magnet is configured to correspond to the required configuration to bring the cyclotron to standard operation at step 407. Once the super-conducting magnet sub-system is fully powered after step 407, a proton beam is generated by the ion source at step 409. Once the beam is generated, the proton beam may be extracted out of the cyclotron at step 411 by configuring the beam path of the generated beam. Configuring the beam path of the generated beam may comprise, for example, generating an electric field which directs (or deflects) the trajectory of the beam by applying only a low voltage in the electrostatic vertical deflectors of the vertical deflector sub-system. Accordingly, an extraction of a proton beam from any of the plurality of cyclotron states may be achieved by performance of steps 401-411, directly at the end of the start-up procedure and without the performance of any additional procedures.

In further embodiments, the working point (operational settings) of the cyclotron is tuned by an automated phase control loop at step 413 to ensure the beam quality needed for medical operation of the system. The phase control loop tunes the magnetic field to an operational level by, for example, monitoring an extracted beam in the phase control loop and further tuning the monitored, extracted beam as necessary to conform to a desired configuration. Monitoring the extracted beam may comprise, for example, measuring the time behavior (phase) of the extracted beam with respect to the radio frequency sub-system of the cyclotron in a feedback sub-system or phase measurement system. The phase of the extracted beam may be measured by a non-destructive beam phase detector, for instance. By monitoring the extracted beam, the effects of phase shifts of an extracted beam caused by magnetic field drifts or other influences may be measured and quantified with respect to the RF frequency of the cyclotron. Once the extracted beam is monitored for the effects of phase shifts, the extracted beam may be further tuned to stabilize the effect of the beam phase shifts by resetting the current in the super-conducting magnet to a desired value.

Automated Tuning Procedures for Superconducting Proton Cyclotron

Figure 5:
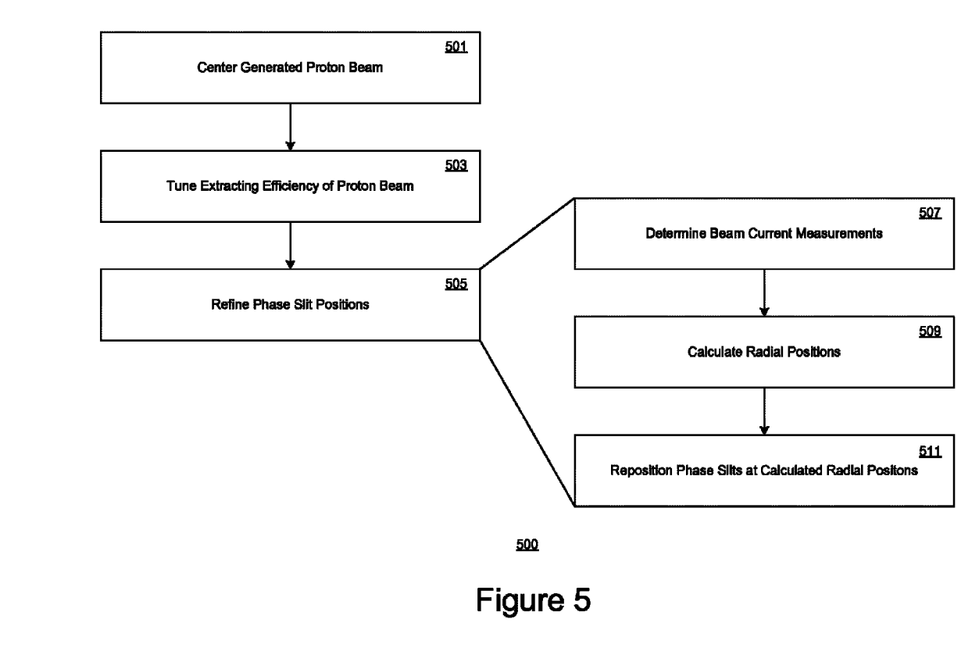
FIG. 5 depicts a flowchart of a method of automatically tuning a proton accelerator, in accordance with embodiments of the claimed subject matter.

After a service action or maintenance routine, a cyclotron may require re-tuning in order to restore an operational configuration of the cyclotron. For example, a service action may cause a displacement or resetting of one or more values or configurations of the various sub-systems and sub-system components to lie outside an operational or desired range. This may cause a generated proton beam with reduced extraction efficiency due to unintentional variations in the positioning of trim rods inside a cyclotron resulting from the performance of a service action or maintenance routine. Other sensitive components such as electrostatic deflectors and phase slits may be similarly impacted during these routines. FIG. 5 depicts an example procedure 500 for automated tuning procedures of a proton cyclotron. The procedure 500 may be performed, for example, after a service action or maintenance routine which requires the removal and/or replacement of physical, hardware components of the cyclotron, for example. Additionally, the procedure 500 may be performed after long periods of inactivity, or to correct a sub-optimal performance of the cyclotron. Steps 501-511 describe exemplary steps of the process 500 in accordance with the various embodiments herein described.

According to process 500, a generated proton beam is automatically centered at step 501. Centering a generated proton beam may be performed by, for example, proper positioning of a plurality of moveable trim rods disposed in the center of the cyclotron. These trim rods are known as the inner trim rods (to be distinguished from outer trim rods placed at the radius of the extraction point) of the cyclotron. In one embodiment, the inner trim rods may comprise eight iron trim rods. Automatically centering the generated proton beam may be performed by measuring an oscillation of the beam current to determine the precession of the generated proton beam. Measuring the oscillation may be performed with an internal straight probe, for example. Once the oscillation is measured, the proton beam may be centered by using the plurality of inner trim rods to adjust the amplitude and phase of the first field harmonic of the generated magnetic field changes to reduce the precession of the generated beam. According to further embodiments, a radial beam probe is used to perform multiple probe scans and calculates proper inner trim rod settings (e.g., positions) based on the data from the scans. Once the settings are determined, the inner trim rods may be automatically positioned to center the proton beam at step 501.

At step 503, an extraction efficiency of the generated proton beam is tuned. The extraction efficiency may be tuned by analyzing the beam current of the extracted beam with respect to the position of the outer trim rods (e.g., the set of movable trim rods placed at the radius of the extraction point in the cyclotron) and the voltages of the one or more electrostatic deflectors ("extraction deflectors") and resetting the position of the outer trim rods and/or voltage of the extraction deflectors to pre-defined values. According to one embodiment, the extraction efficiency may be further tuned by exciting the precession of the generated proton beam prior to the extraction of the proton beam to increase the turn separation of the particles in the proton beam at the electrostatic deflectors. Exciting the precession of the generated proton beam may be performed by positioning of the outer trim rods, for example.

At step 505, the positions of a plurality of radial phase slits (e.g., phase slits 306) are refined. The positions of the plurality of radial phase slits 306 may be refined by, for example, determining a plurality of beam current measurements taken at the plurality of phase slits at a first radial position, calculating a preferred or better performing configuration of the plurality of phase slits at a second radial position, and automatically re-positioning the plurality of phase slits to the second radial position. By re-positioning the plurality of phase slits to a second, better performing radial position, internal beam losses can be reduced.

By using the automatic procedures described above for the initialization and tuning of a cyclotron, operation of a cyclotron from an off or reduced power state to a fully configured, operational state may be performed with greatly improved efficiency, and requiring only minimal oversight.

Although the subject matter has been described in language specific to structural features and/or processological acts, it is to be understood that the subject matter defined in the appended claims is not necessarily limited to the specific features or acts described above. Rather, the specific features and acts described above are disclosed as example forms of implementing the claims.

What is claimed is:

1. A system comprising:
   a proton therapy system comprising a plurality of sub-systems including:
      a magnet sub-system;
      a cooling sub-system;
      a vacuum sub-system;
      a radio frequency sub-system;
      an beam injection sub-system;
      a beam extraction sub-system; and
      a feedback sub-system,
   wherein an operation of the proton therapy system comprises at least one operation state, the at least one operation state corresponding to one of a plurality of power states of one of the plurality of sub-systems,
   wherein the proton therapy system is configured to enter at least one of the plurality of operation states to prepare the proton therapy system to generate and extract a proton beam.

2. The system of claim 1, wherein the plurality of operation states activate the plurality of sub-systems in sequence.

3. The system of claim 1, wherein the plurality of operation states comprise an off state, a first standby state, a second standby state, a radio frequency ready state and a beam ready state.

4. The system of claim 3, wherein the off state comprises a proton therapy system operation state wherein each of the plurality of sub-systems are deactivated.

5. The system of claim 3, wherein the first standby state comprises a proton therapy system operation state wherein the cooling sub-system and vacuum sub-systems are activated and all other sub-systems of the plurality of sub-systems are deactivated.

6. The system of claim 3, wherein the second standby state comprises a proton therapy system operation state wherein the magnet sub-system, the cooling sub-system, and the vacuum sub-system are activated and all other sub-systems of the plurality of sub-systems are deactivated.

7. The system of claim 3, wherein the radio frequency ready state comprises a proton therapy system operation state wherein the magnet sub-system, the cooling sub-system, the vacuum sub-system, and the radio frequency sub-system are activated, and all other sub-systems of the plurality of sub-systems are deactivated.

8. The system of claim 7, wherein the radio frequency sub-system is activated in a reduced power state during the radio frequency ready state.

9. The system of claim 3, wherein the beam ready state comprises a proton therapy system operation state wherein each of the plurality of sub-systems are activated and operating at a plurality of pre-defined set values.

10. The system of claim 1, wherein the plurality of sub-systems further comprises a deflector plate sub-system configured to generate an electric field in a plurality of deflector plates comprised in the cyclotron to influence a trajectory of the proton beam extracted from the proton therapy system.

11. The system of claim 10, wherein the electric field is generated in the plurality of deflector plates by supplying a voltage through the deflector plates.

12. The system of claim 1, wherein the plurality of sub-systems further comprises a phase measurement sub-system comprised in the proton therapy system and configured to correct an effect of beam phase shifts affecting the proton beam.

13. The system of claim 12, wherein the a phase measurement sub-system comprises a non-destructive beam phase detector.

14. The system of claim 12, wherein the a phase measurement sub-system comprises a phase control loop configured to tune a magnetic field generated by the magnet sub-system.

15. The system of claim 14, wherein the phase control loop tunes the magnetic field generated by the magnet sub-system by measuring the effect of the beam phase shifts affecting the proton beam with respect to a radio frequency generated by the radio frequency sub-system during operation of the proton therapy system.

16. The system of claim 1, wherein the proton therapy system comprises a cyclotron.

17. A method for automatic cyclotron initialization comprising:
   measuring a temperature of a plurality of components in a magnet comprised in a cyclotron;
   determining a current configuration of the magnet based on the temperature;
   automatically setting a power supply of the magnet to the determined current configuration;

generating a proton beam in an beam injection component comprised in the cyclotron with a magnet operating with the determined current configuration; and extracting the proton beam through a plurality of radial slits.

18. The method of claim 17 further comprising monitoring the extracted proton beam in a phase control loop.

19. The method of claim 18 wherein the extracted proton beam comprises a beam phase, and wherein monitoring the extracted proton beam comprises measuring the beam phase with respect to a radio frequency system of the cyclotron in a phase measurement system.

20. The method of claim 19 wherein monitoring the beam comprises utilizing a signal of a non-destructive beam phase detector.

21. The method of claim 19 further comprising tuning the extracted proton beam monitored in the phase control loop.

22. The method of claim 19 wherein monitoring the beam comprises measuring and quantifying an effect of beam phase shifts due to magnetic field drifts.

23. The method of claim 22 wherein tuning the beam comprises tuning ai a beam current stability of the cyclotron by stabilizing the effect of the beam phase shifts due to magnetic field drifts.

24. The method of claim 22 wherein tuning the beam comprises resetting the magnet current to a desired value.

25. A method for automatically refining operation of a cyclotron, the method comprising:
centering a proton beam produced by the cyclotron by variably positioning a plurality of magnetic rods comprised in the cyclotron;
tuning an extraction efficiency of the proton beam produced by the cyclotron; and
refining positions of a plurality of radial slits comprised in the cyclotron,
wherein the centering, the tuning and the refining are performed automatically by a control system of the cyclotron.

26. The method according to claim 25 wherein automatically centering the proton beam comprises:
measuring an oscillation of a current of the proton beam to determine a precession of the proton beam; and
reducing the precession of the proton beam.

27. The method according to claim 26, wherein the oscillation of the current is measured by an internal straight probe.

28. The method according to claim 26, wherein reducing the precession of the radial beam comprises using the first plurality of magnetic rods to adjust an amplitude and a phase of a first harmonic of the generated magnetic field corresponding to the oscillation of the current of the proton beam.

29. The method according to claim 25, wherein automatically tuning an extraction efficiency comprises analyzing a beam current of the proton beam and resetting values corresponding to a second plurality of trim rods and voltages in a plurality of extraction deflectors to pre-defined values.

30. The method according to claim 29, wherein automatically tuning an extraction efficiency further comprises exciting the precession of the proton beam prior to an extraction of the proton beam with a second plurality of trim rods.

31. The method according to claim 29, wherein automatically tuning an extraction efficiency further comprises adjusting the voltages in a plurality of extraction deflectors, the plurality of extraction deflectors configured to direct a trajectory of the extracted proton beam.

32. The method according to claim 25, wherein the automatically refining positions for the plurality of radial slits comprises:
determining a plurality of beam current measurements at the plurality of slits, the plurality of slits being positioned at a first plurality of radial positions;
calculating a second plurality of radial positions based on the plurality of beam current measurements; and
automatically re-positioning the slits at the second plurality of radial positions.

33. The system according to claim 1, wherein the beam extraction sub-system comprises at least one of:
a plurality of interconnecting tubes; and
a plurality of radial slits.

34. The system according to claim 12, wherein the feedback sub-system is configured to measure and quantify an effect of beam phase shifts incurred by the proton beam due to drifts in the magnetic fields generated by the magnetic sub-system.

35. The system according to claim 34, wherein the phase measurement sub-system is configured to correct the effect of beam phase shifts measured by the feedback sub-system.

36. The system according to claim 1, wherein the magnetic sub-system comprises at least one of:
a plurality of trim coils; and
a plurality of trim rods.

* * * * *